United States Patent
Barry et al.

(10) Patent No.: US 6,476,295 B2
(45) Date of Patent: *Nov. 5, 2002

(54) EXPRESSION OF SUCROSE PHOSPHORYLASE IN PLANTS

(75) Inventors: Gerard Francis Barry, St. Louis, MO (US); Jan Willem de Weerd, Meridian, ID (US); Ganesh Murthy Kishore, Chesterfield; Marcia Lee Weldon, Bonne Terre, both of MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/797,467

(22) Filed: Mar. 1, 2001

(65) Prior Publication Data

US 2001/0016953 A1 Aug. 23, 2001

Related U.S. Application Data

(63) Continuation of application No. 09/020,818, filed on Feb. 9, 1998, now Pat. No. 6,222,098, which is a continuation of application No. 08/596,024, filed on Feb. 6, 1996, now Pat. No. 5,716,837, which is a continuation-in-part of application No. 08/386,860, filed on Feb. 10, 1995, now abandoned.

(51) Int. Cl.$^7$ .................. C12N 15/82; C12N 15/52; C12N 5/04; A01H 5/00; A01H 5/10; C12P 19/00
(52) U.S. Cl. ................ 800/284; 800/317.2; 800/320.1; 800/320.2; 800/317.4; 800/320; 800/298; 800/315; 800/316; 800/278; 800/320.3; 435/468; 435/419; 435/417; 435/411; 435/412
(58) Field of Search .................. 800/278, 284, 800/260, 298, 317.2, 320, 320.1, 315, 320.2, 316, 320.3, 317.4; 536/102, 1.11, 23.1; 530/370; 435/419, 468, 417, 411, 412, 430

(56) References Cited

U.S. PATENT DOCUMENTS

| | | | |
|---|---|---|---|
| 4,770,710 A | * | 9/1988 | Friedman et al. ............. 127/29 |
| 4,888,170 A | | 12/1989 | Curtiss, III .................. 424/93 |
| 5,349,123 A | | 9/1994 | Shewmaker et al. ......... 800/205 |
| 5,716,837 A | * | 2/1998 | Barry et al. .............. 435/240.4 |
| 6,222,098 B1 | * | 4/2001 | Barry et al. ................. 800/284 |
| 6,235,971 B1 | * | 5/2001 | Barry et al. ................. 800/278 |

FOREIGN PATENT DOCUMENTS

| | | |
|---|---|---|
| EP | 0 442 592 | 8/1991 |
| EP | 0 634 491 | 1/1995 |
| WO | WO 90/02484 | 3/1990 |
| WO | WO 90/12084 | 10/1990 |
| WO | WO 91/19806 | 12/1991 |
| WO | WO 92/14831 | 9/1992 |
| WO | WO 93/06711 | 4/1993 |
| WO | WO 95/02696 | 1/1995 |

OTHER PUBLICATIONS

Russell et al., *Infection and Immunity*, vol. 56, No. 10, "*Streptococcus mutans* gtfA Gene Specifies Sucrose Phosphorylase," pp. 2763–2765 (1988).

James et al., *Nucleic Acids Research*, vol. 16, No. 21, "Nucleotide sequence of the gtfA gene from *S.mutans* GS–5*," p. 10398 (1988).

Ferretti et al., *Infection and Immunity*, vol. 56, No. 6, "Sequence Analysis of the GlucosyltransferaseA Gene (gtfA) from *Streptococcus mutans* Ingbritt," pp. 1585–1588 (1988).

* cited by examiner

*Primary Examiner*—David T. Fox
*Assistant Examiner*—Anne Kubelik
(74) *Attorney, Agent, or Firm*—Howrey Simon Arnold & White, LLP; Thomas McBride

(57) ABSTRACT

Introducing sucrose phosphorylase activity into plants by transformation with a gene for the enzyme increases the rate of sucrose hydrolysis, leading to increased starch, oil, and protein levels. The preferred gene is from *Streptococcus mutans*. Surprisingly, in potatoes transformed to express this gene in tubers, reduced bruise discoloration susceptibility and increased uniformity of starch deposition throughout the tuber are achieved.

5 Claims, No Drawings

SEQUENCE LISTING

<160> NUMBER OF SEQ ID NOS: 5

<210> SEQ ID NO 1
<211> LENGTH: 29
<212> TYPE: DNA
<213> ORGANISM: Artificial
<220> FEATURE:
<223> OTHER INFORMATION: Synthetic

<400> SEQUENCE: 1
cccggatcca tggcaattac aaataaaac          29

<210> SEQ ID NO 2
<211> LENGTH: 39
<212> TYPE: DNA
<213> ORGANISM: Artificial
<220> FEATURE:
<223> OTHER INFORMATION: Synthetic

<400> SEQUENCE: 2
ggggagctca ctcgaagctt attgtttgat cattttctg          39

<210> SEQ ID NO 3
<211> LENGTH: 1478
<212> TYPE: DNA
<213> ORGANISM: Genomic

<400> SEQUENCE: 3
agccttgtgt taggggtat tcaaaccttc tttgactgaa aattttatta tttatacatg      60
tttaaaatta cttttaatc tatatataat agatatcaat ccttcattta attgtatttt    120

```
tgtattaatt ctataaatat taaattactt tattaaaaat tctaattctg tcactcgtca    180
tttcataata ttcttgacgg tgatggtagt gataattacg ttgattggag ccacatgggc    240
cgctactttt taaaaggatg aaccttggaa tgtagtgaat gttgagtctc atagctcact    300
cacggactca acagcaaaat ctgtcctctt tttcccttct ccaattcaca tactgtcact    360
tggacaaata atatttgaaa attttggcct aaagttaggt ttggagccgt atggtaattt    420
gatacacaaa ttattatata attgatatat caggtatata tatcaagttg tcgcttcttc    480
gttcattgtt tctctcacta aaattttcaa ttcacttttt aaaaaatcga taaatttta    540
atataacttt acataacata ttcaaaatta caaaaataaa ggatattttt atatgtttat    600
ttttaatgta agattaaata tttagaattc tttttaagaa cggtacaagc aaattaaaag    660
agagaaggta tattagtggg cctatgtatc tttgatatca tatgcctctc aaagagcatc    720
ctgatgagtc tatatatctt tgttgatagt gatttaacca tttatgtatg tacgtagtac    780
taagacatgt taaataagat cctagagaaa gattttttgga aaagtgaaaa cagcaataaa    840
gaaaagtcat ttaaacactt tccaacaaac atttggtaat cgattttaat tacccactta    900
aacaaaacta tttgtacgta aaatgtttaa gtagaaaaga gattttttta aaaaaaaaa    960
gaaggcaaga ggtcatatat ctgacccttc cttaaatccc cgcgtataac actttctttt    1020
ttttgtgtgt gtatgttcag gaacatttgt attttctatt tgaaatttct cattaagtca    1080
aattcgaaat cttttaaata atgtagagaa atctcattat atttaacaat cccacttgat    1140
gaattcctaa acatttttcta taaataaca ctaaatcttt aattatacat attacatacc    1200
taactcaagc aatcttgtcg gaaaaatcat tagaaaagaa ttggaaatag ggaaataaat    1260
agacatattt tggttagtat ctttgtctat aagaatgggt gtgttaaaga gctagtgcca    1320
tagtgtacca ttctattggt agcatttggc aagagttatt ccctctctcc ataccaatgg    1380
agaagtttaa tcttgctaga gtcttattgt tgcttcttca acttggaact ttgttcattg    1440
cccatgcatg tccttattgt ccatatcctc cttccacc                           1478
```

<210> SEQ ID NO 4
<211> LENGTH: 450
<212> TYPE: DNA
<213> ORGANISM: Genomic

<400> SEQUENCE: 4

```
aaataaatat ttcaaagtaa attgttactc cctctatccc atactctttt cttttttaa    60
tcgatttctt actctaattg aactattgga gacaacttaa atgtaaattt ttttttctt    120
tatcaaaatg attggctgct atataaatat ctaatggtta ttatacataa attttaatat    180
tttttataaa aaaatatcga gctaaatcat atcgtttaaa tatagagatg tgttattat    240
ttaaaaatta attttaaaaa agtgaatatt gtaaattagg atgaaagagt attatattgg    300
ttgtcgcagt ataaataccc tgcatgccat tacatttgtt caatcatctt tgcaacgatt    360
tgtgtgcttt agcttcctta cataacatgg cttctataac taaagcctca ttacttatcc    420
ttttcctctc cttgaatctc ctttctcttcg                                     450
```

<210> SEQ ID NO 5
<211> LENGTH: 1446
<212> TYPE: DNA
<213> ORGANISM: Genomic

<400> SEQUENCE: 5

-continued

```
atggcaatta caaataaaac aatgttgatt acttacgcag acagtttggg taaaaatttg      60
aaagaattga atgaaaatat tgagaattat tttgcagatg ctgttggcgg tgtccatttg     120
ctgccattct ttccttccac aggtgatcgt ggctttgcac cgattgatta ccatgaagtt     180
gactctgctt ttggcgattg ggatgatgtc aaacgtttgg gtgaaaaata ttacctcatg     240
tttgatttca tgattaatca tatttcgcgt cagtctaaat attataaaga ttaccaagaa     300
aagcatgaag caagtgctta taaagatcta tttttaaatt gggataaatt ttggcctaaa     360
aatcgcccga cacaagaaga tgtggacctg atttataagc gtaaggatcg agcacctaag     420
caggaaatcc aatttgcaga tggcagtgtt gaacatctct ggaacacttt tggggaggaa     480
cagattgatc ttgacgtgac taaagaagtg actatggatt ttattcgctc taccattgaa     540
aatttagcag ccaacggctg tgatctcatt cgtttggatg cctttgctta tgctgttaaa     600
aagctagata cgaatgattt ctttgttgaa cctgaaatct ggactctgct agataaagtt     660
cgtgatatag ctgctgtatc gggtgcggaa atcttgccgg aaattcatga acactatact     720
attcaattta aaattgcaga ccatgattac tatgtttatg attttgccct gcctatggtg     780
acgctctaca gcctatattc gggcaaggtt gaccgtcttg ccaaatgggt gaaaatgagt     840
ccgatgaaac agttcaccac ccttgataca catgacggta ttggtgtggt tgatgttaag     900
gatatcctga ctgacgaaga aattacctat acttctaatg agctttataa ggtcggtgcc     960
aatgtcaatc gtaagtattc aactgccgaa tataataact tggatatcta tcaaattaat    1020
tcaacttact attcagcact tggtgatgat gatcaaaaat acttttttggc ccggttgata    1080
caagcttttg ctccaggtat tccacaggtt tattacgttg gctttttagc tggcaagaat    1140
gatcttgaat tactggaaag cactaaagaa ggccgcatta tcaaccgtca ttattatagt    1200
agtgaagaaa ttgctaagga agtgaagcgg ccagttgtca aggcactttt aaatctcttt    1260
acttaccgca ttcagtcagc agcttttgat ttggatggcc gtattgaagt ggaaacgcca    1320
aatgaagaga acattgtcat agaacgtcaa aataaagatg gcagtcatat cgcaacagca    1380
gagattaatc tccaagatat gacatacaga gtaacagaaa atgatcaaac aataagcttc    1440
gagtga                                                               1446
```

EXPRESSION OF SUCROSE PHOSPHORYLASE IN PLANTS

This is a continuation of application Ser. No. 09/020,818 filed Feb. 9, 1998 now U.S. Pat. No. 6,222,098, which is a continuation application of Ser. No. 08/596,024 filed Feb. 6, 1996, which issued on Feb. 10, 1998 (U.S. Pat. No. 5,716, 837), which is a continuation in part of application Ser. No. 08/386,860, filed Feb. 10, 1995, now abandoned.

Recent advances in genetic engineering have provided the requisite tools to transform plants to contain foreign genes. It is now possible to produce plants which have unique characteristics of agronomic and crop processing importance. Certainly, one such advantageous trait is enhanced starch and/or solids content and quality in various crop plants. Another is enhanced oil and protein content of seeds of various crop plants.

Sucrose is the carbon storage unit which is transported from the source tissues of most plants to the sink tissues. In sink tissues it is hydrolyzed and the components used to build other, more complex storage units, primarily starch, protein, and oil. The hydrolysis is primarily accomplished by sucrose synthase which produces UDPglucose and fructose. UDPglucose is converted to glucose 1-phosphate by UDPglucose pyrophosphorylase.

The starch content of the sink tissues of various crop plants has been increased through the use of a gene encoding a bacterial ADPglucose pyrophosphorylase. See PCT Application WO 91/19806 (equivalent to U.S. Ser. No. 08/120, 703, Kishore, incorporated herein by reference). This enzyme catalyzes the production of ADPglucose from glucose 1-phosphate. It has also been found that its expression during certain phases of seed development can decrease the oil content which is thought to be due to the shunting of raw material to the starch pathway with a concomitant decrease in its availability for oil production.

Bruising of potatoes is a phenomenon found during large-scale production, handling, and storage. The bruise is seen as a dark spot primarily in the cortex area of the tuber. Bruising can lead to loss of quality in the tuber, lower consumer acceptance of potatoes and potato products, and processing loss of tubers having excessive levels of bruising. It has been found that potato varieties with higher starch content have greater susceptibility to bruising. It would be desirable to decrease the level or incidence of bruising and particularly desirable to do so while increasing the starch content of the tuber.

A more uniform distribution of starch and solids within the potato tuber is also desirable. The pith or core of the potato generally has lower solids content that the outer or cortex region. When longitudinal strips are cut from the potato tuber to make french fries, the middle portions of these strips therefore have lower solids levels than the ends and this is especially true of strips cut from the center of the tuber. Strips with lower solids content or with regions of lower solids content require longer cooking times to achieve the same degree of acceptability to the consumer. These longer cooking times may result in over-cooking of the higher solids strips. Longer frying times also result in greater absorption of fat and therefore low solids strips and those with lower solids content regions will have a higher fat content. Higher fat content fries are a less nutritious food. In the manufacture of potato chips, slices are cut across the potato tuber and the non-uniform distribution of solids can result in a fried product with over-cooked edges, under-cooked centers, and a higher fat content (especially in the center). The non-uniform distribution of solids in the potato tuber also results in disproportionate losses of potato solids (from the cortex) during the peeling process.

Higher solids content is also desirable in tomato. Higher solids in the form of soluble (usually sugars and acids) and insoluble solids contribute to processing efficiency and the yield of products such as ketchup, paste, sauces, and salsa. These solids also contribute to the taste and texture of the processed products. Higher solids also contribute to the improved taste of fresh tomatoes.

Sucrose phosphorylase is a microbial enzyme which catalyzes production of glucose-1-phosphate directly from sucrose. Its activity has been observed in a wide range of bacterial and fungal species, and the enzyme has been isolated from a number of them (Pimentel et al., 1992; Vandamme et al., 1987). Genes for this enzyme, have been isolated from Agrobacterium spp. (Fournier et al., 1994, and references cited therein), *Streptococcus mutans*, denominated gtfA, (Russell et al., Perry et al.) and *Leuconostoc mesenteroides*, denominated spl (Kitao et al., 1992). Heterologous expression of the gene from *S. mutans* in *E. coli* is disclosed in U.S. Pat. No. 4,888,170 (Curtiss, 1989), incorporated herein by reference. The utility of the transformed microorganism is use as a vaccine against *S. mutans*.

It is an object of this invention to provide an improved means for increasing starch content of various plants. It is a still further object to provide a means of decreasing the sucrose content of seeds in oilseed crops resulting in a decrease in the level of undesirable carbohydrates such as stachyose and raffinose, while increasing the carbon available for oil and protein production. It is a still further object to provide novel DNA constructs which are useful in providing said means. It is a still further object to provide potato tubers which exhibit increased starch content more uniformly throughout the tuber. It is a still further object of this invention to provide potato tubers with a reduced susceptibility to bruising. It is a still further object of this invention to provide improved cereal crops, such as maize, rice, wheat, and barley.

SUMMARY OF THE INVENTION

The present invention provides DNA constructs which encode a sucrose phosphorylase (SP) enzyme and which are useful in producing enhanced starch content in plants. In another aspect of the present invention, seeds having a decreased level of sucrose and other carbohydrates, which will result in increased oil and protein, content as a result of SP expression are provided.

In accomplishing the foregoing, there is provided, in accordance with one aspect of the present invention, a method of modifying the carbohydrate content of target tissues of transgenic plants, comprising the steps of:
(a) inserting into the genome of a plant cell a recombinant, double-stranded DNA molecule comprising in sequence
  (i) a promoter which functions in the cells of a target plant tissue,
  (ii) a structural DNA sequence that causes the production of an RNA sequence which encodes a sucrose phosphorylase enzyme,
  (iii) a 3' non-translated DNA sequence which functions in plant cells to cause transcriptional termination and the addition of polyadenylated nucleotides to the 3' end of the RNA sequence;
(b) obtaining transformed plant cells; and
(c) regenerating from the transformed plant cells genetically transformed plants.

In another aspect of the present invention there is provided a recombinant, double-stranded DNA molecule comprising in sequence (i) a promoter which functions in the cells of a target plant tissue, (ii) a structural DNA sequence that causes the production of an RNA sequence which encodes a sucrose phosphorylase enzyme, (iii) a 3' non-translated DNA sequence which functions in plant cells to cause transcriptional termination and the addition of polyadenylated nucleotides to the 3' end of the RNA sequence.

There have also been provided, in accordance with another aspect of the present invention, transformed plant cells that contain DNA comprised of the above-mentioned elements (i), (ii), and (iii). In accordance with yet another aspect of the present invention, differentiated potato, tomato, and cereal plants are provided that have increased starch content in the tubers, fruit and seeds, respectively, and differentiated oilseed crop plants are provided that have decreased sucrose and oligosaccharides containing sucrose, such as stachyose and raffinose, in the seeds.

There have also been provided methods of increasing the starch content in the starch production organs of plants, such as the tuber of potato and the seed of cereals, and decreasing the sucrose levels in oilseed crop plants, such as soybean and canola, leading to increased oil and protein content. In carrying out the method in potato, it has unexpectedly been found that there is a more uniform distribution of starch as compared between the pith and the cortex of the tuber. In another aspect of the invention, a method of providing potatoes having a reduced susceptibility to bruising is provided.

An additional advantage of sucrose phosphorylase activity in sink tissue, such as the tuber of potato, is related to providing an increased, novel sucrose hydrolyzing activity having a much lower $K_m$ for sucrose (1–25 mM) than that for plant sucrose hydrolyzing enzymes—sucrose synthases and invertases, which have a $K_m$ in the range of 50–300 mM. This advantage is important in the establishment of and strength of such sink tissues resulting potentially in yield enhancement.

DETAILED DESCRIPTION OF THE INVENTION

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT publication WO 84/02913 (Rogers et al., Monsanto).

Promoters which are known or are found to cause transcription of DNA in plant cells can be used in the present invention. Such promoters may be obtained from a variety of sources such as plants and plant viruses and include, but are not limited to, the enhanced CaMV35S promoter and promoters isolated from plant genes such as ssRUBISCO genes. As described below, it is preferred that the particular promoter selected should be capable of causing sufficient expression to result in the production of an effective amount of sucrose phosphorylase (SP) enzyme to cause the desired increase in starch content. In addition, it is preferred to bring about expression of the SP gene in specific tissues of the plant such as root, tuber, seed, fruit, etc. and the promoter chosen should have the desired tissue and developmental specificity. Those skilled in the art will recognize that the amount of sucrose phosphorylase needed to induce the desired increase in starch content may vary with the type of plant and furthermore that too much sucrose phosphorylase activity may be deleterious to the plant. Therefore, promoter function should be optimized by selecting a promoter with the desired tissue expression capabilities and approximate promoter strength and selecting a transformant which produces the desired sucrose phosphorylase activity in the target tissues. This selection approach from the pool of transformants is routinely employed in expression of heterologous structural genes in plants since there is variation between transformants containing the same heterologous gene due to the site of gene insertion within the plant genome. (Commonly referred to as "position effect").

It is preferred that the promoters utilized in the double-stranded DNA molecules of the present invention have relatively high expression in tissues where the increased starch content and/or dry matter is desired, such as the tuber of the potato plant, the fruit of tomato, or seed of maize, wheat, rice, and barley. Expression of the double-stranded DNA molecules of the present invention by a constitutive promoter, expressing the DNA molecule in all or most of the tissues of the plant, will be rarely preferred and may, in some instances, be detrimental to plant growth.

The class I patatin promoter has been shown to be both highly active and tuber-specific (Bevan et al., 1986; Jefferson et al., 1990). A sequence of ~1.0 kb portion of the tuber-specific class I patatin promoter is preferred for tuber expression in the present invention. A number of other genes with tuber-specific or—enhanced expression are known, including the potato tuber ADPGPP genes, both the large and small subunits, (Muller et al., 1990), sucrose synthase (Salanoubat and Belliard, 1987, 1989), the major tuber proteins including the 22 kd protein complexes and proteinase inhibitors (Hannapel, 1990), the granule bound starch synthase gene (GBSS) (Rohde et al., 1990), and the other class I and II patatins (Rocha-Sosa et al., 1989; Mignery et al., 1988). Other promoters which are contemplated to be useful in this invention include those that show enhanced or specific expression in potato tubers, that are promoters normally associated with the expression of starch biosynthetic or modification enzyme genes, or that show different patterns of expression within the potato tuber. Examples of these promoters include those for the genes for the granule-bound and other starch synthases, the branching enzymes (Kossmann et al., 1991; Blennow, A. and Johansson, G., 1991; WO 92/14827; WO 92/11375), diproportionating enzyme (Takaha et al., 1993), debranching enzymes, amylases, starch phosphorylases (Nakano et al., 1989; Mori et al., 1991), pectin esterases (Ebbelaar, et al., 1993), the 40 kD glycoprotein, ubiquitin, aspartic proteinase inhibitor (Stukerlj et al., 1990), the carboxypeptidase inhibitor, tuber polyphenol oxidases (Shahar et al., 1992; GenBank® Accession Numbers M95196 and M95197), putative trypsin inhibitor and other tuber cDNAs (Stiekema et al., 1988), and for β-amylase and sporamins (from *Ipomoea batatas*; Yoshida et al., 1992; Ohta et al., 1991).

In addition, promoters may be identified to be tuber specific by screening a cDNA library of potato for genes which are selectively or preferably expressed in tubers and then determine the promoter regions to obtain tuber selective or tuber-enhanced promoters.

Other promoters can also be used to express a sucrose phosphorylase gene in specific tissues, such as seeds or fruits. β-conglycinin (also known as the 7S protein) is one of the major storage proteins in soybean (*Glycine max*) (Tierney, 1987). The promoter for β-conglycinin or other seed-specific promoters such as the napin and phaseolin promoters, can be used to over-express an SP gene specifically in seeds. This would lead to a decrease in the sucrose content of the seeds, which will result in a decrease in undesirable oligosaccharides and potentially an increase in the oil and/or protein content, which would be desirable in seeds used for oil or protein production such as soybean, canola, oilseed rape, sunflower, safflower, etc. The SP gene will provide more raw material more quickly, but the plants own regulatory mechanisms will, unless influenced by other enzymes produced from heterologous genes, direct its use in the sink tissues.

The zeins are a group of storage proteins found in maize endosperm. Genomic clones for zein genes have been isolated (Pedersen, 1982), and the promoters from these clones, including the 15 kD, 16 kD, 19 kD, 22 kD, 27 kD, and gamma genes, could also be used to express an SP gene in the seeds of maize and other plants. Other promoters known to function in maize include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression of an SP gene is the promoter for a glutelin gene from rice, more particularly the Osgt-1 promoter (Zheng et al., 1993).

If one wanted to increase oil in maize seed, rather than starch, one would choose a promoter which causes expression of the SP gene during oil deposition. Such a promoter would be activated during the formation of the plant embryo. Examples of promoters active during embryogenesis are the promoters from the genes for globulin 1 and the late embryogenesis active (lea) proteins.

Examples of promoters suitable for expression of an SP gene in wheat include those for the genes for the ADPglucose pyrophosphorylase (ADPGPP) subunits, for the granule bound and other starch synthases, for the branching and debranching enzymes, for the embryogenesis-abundant proteins, for the gliadins, and for the glutenins. Examples of such promoters in rice include those for the genes for the ADPGPP subunits, for the granule bound and other starch synthases, for the branching enzymes, for the debranching enzymes, for sucrose synthases, and for the glutelins. A particularly preferred promoter is the promoter for rice glutelin, Osgt-1. Examples of such promoters for barley include those for the genes for the ADPGPP subunits, for the granule bound and other starch synthases, for the branching enzymes, for the debranching enzymes, for sucrose synthases, for the hordeins, for the embryo globulins, and the aleurone specific proteins.

The solids content of tomato fruit can be increased by expressing an SP gene behind a fruit specific promoter. The promoter from the 2A11 genomic clone (Pear, 1989) will control expression of ADPglucose pyrophosphorylase in tomato fruit. The E8 promoter (Deikman, 1988) would also express the SP gene in tomato fruits. In addition, promoters which function during the green fruit stage of tomatoes are disclosed in PCT Application PCTUS94/07072, filed Jun. 27, 1994, designating the U.S., incorporated herein by reference. They are designated TFM7 and TFM9. TFM7 which is a DNA fragment, isolated from tomato, of about 2.3 kb, of which 1.4 kb of the 3' end is shown in SEQ ID NO:3. TFM9 which is a DNA fragment of about 900 bp, of which 400 bp of the 3' end is shown in SEQ ID NO:4.

It is also now known that potato tuber promoters will function in tomato plants to cause fruit specific expression of an introduced gene. (See U.S. Ser. No. 08/344,639, Barry et al., filed Nov. 4, 1994, incorporated herein by reference.) Such promoters include potato patatin promoters, potato ADPGPP promoters, and potato granule bound starch synthase promoters. A particularly preferred promoter for tomato fruit expression is the promoter for the gene encoding the small subunit of ADPGPP in potato.

The solids content of root tissue can be increased by expressing an SP gene behind a root specific promoter. The promoter from the acid chitinase gene (Samac et al., 1990) would express the SP gene in root tissue. Expression in root tissue could also be accomplished by utilizing the root specific subdomains of the CaMV35S promoter that have been identified (Benfey et al., 1989).

The RNA produced by a DNA construct of the present invention may also contain a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

Targeting Signal Sequences

An alternative method of increasing the rate of sucrose hydrolysis would be to target the SP to the apoplast. To do so requires a signal peptide is required on the N'-terminus of the functional protein. A preferred example of a sequence encoding such a signal sequence is a plant endoplasmic reticulum signal sequence from the PR-1B protein (Ohshima, et al., 1990). Thus the SP would be active in the apoplast and allow sucrose to be hydrolyzed extracellularly and allow for faster transport of glucose into the cell.

Another alternative is to target the SP to the vacuolar space. Targeting of the SP to the vacuole of a plant cell requires information in addition to the signal peptide (Nakamura and Matsuoka, 1993). A prepro-signal peptide could be fused to the amino terminus of the FT to target the enzyme to the vacuole (Sonnewald et al., 1991).

Alternatively, a carboxy terminal sequence extension could be combined with an ER signal sequence to target the enzyme to the vacuole.

Sucrose Phosphorylases

As used herein, the term "sucrose phosphorylase" means an enzyme which catalyzes a reversible conversion of sucrose and inorganic phosphate to α-D-glucose-1-phosphate and D-fructose. It may be isolated from many microbial sources, including *Streptococcus mutans, Clostridium pasteurianum* (Vandamme et al., 1987), *Pseudomonas saccharophila* (Silverstein et al.), *Pseudomonas putrifaciens, Pullularia pullulans, Acetobacter xylinum* (Vandamme et al., 1987), Agrobacterium sp. (Fournier et al., 1994), and *Leuconostoc mesenteroides*.

The gene for the SP enzyme may be obtained by known methods and has already been done so from several organisms, such as Agrobacterium sp. (Fournier et al., 1994) and *Leuconostoc mesenteroides* (Kitao et al., 1992). The gene from *S. mutans* has been expressed in *E. coli* (Robeson et al., 1983, identifying the activity as a glucosyl transferase). The isolation of a gene from *Streptococcus mutans* is described in the Examples below. Its sequence is given as SEQ ID NO:5. This gene can be used as isolated by inserting it into plant expression vectors suitable for the transformation method of choice as described below.

A gene encoding SP (ORF 488) has been identified in the Ti plasmids of *Agrobacterium vitus* (formerly *A. tumefaciens* biotype 3). Related sequences have been reported in the Ti plasmids of other *A. tumefaciens* strains, in particular pTiC58 (Fournier et al., 1994). It is likely that a gene encoding SP may be found on all such plasmids.

Purification of the SP enzyme has been demonstrated from other bacterial and fungal sources (described above). The availability of such materials renders facile the subsequence cloning of the gene for this enzyme: the protein may be used an immunogen to raise antibodies that may be used to identify clones in expression-based libraries such as λgt11 (Sambrook et al.); peptide sequences at the N-terminus of such proteins may be obtained by routine protein sequencing; and, following well established limited proteolysis procedures, the sequences of internal regions may also be determined. Such sequences may be used in the design of nucleotide probes or primers that may be used to identify the genes from clone banks or to amplify the gene or portions of the gene from RNA, cDNA, or DNA preparations from the source organism. Detection of *E. coli* containing sucrose phosphorylase clones is also possible by growth on minimal medium with sucrose as the sole carbon source (Ferretti, et al. 1988).

Other microorganisms that use SP to hydrolyze sucrose can be found by assaying for organisms which can utilize sucrose as the sole carbon source (Russell et al.). The protein can be isolated by following the enzymatic activity in the fractions using known methods. The gene encoding the protein can then be isolated as just described.

Thus, many different genes which encode an protein having sucrose phosphorylase activity may be isolated and used in the present invention.

Polyadenylation Signal

The 3' non-translated region of the chimeric plant gene contains a polyadenylation signal which functions in plants to cause the addition of polyadenylate nucleotides to the 3' end of the RNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene. An example of a preferred 3' region is that from the ssRUBISCO gene of pea, also known as the E9 3' region.

Synthetic Gene Construction

The SP gene from *Streptococcus mutans* is high in A+T content, which may be inimical to high level expression in plant cells, although as shown below, the gene is expressed at levels sufficient to positively affect starch content. If desired, the gene sequence of the SP gene can be changed without changing the protein sequence in such a manner as may increase expression, and thus even more positively affect starch content in transformed plants. The rules for making the changes in the gene sequence are set out in WO 90/10076 (Fischhoff et al.). A gene synthesized by following the rules set out therein may be introduced into plants as described below and result in higher levels of expression of the SP enzyme. This may be particularly useful in monocots such as maize, rice, wheat, and barley.

Combinations with Other Transgenes

The effect of SP in transgenic plants can be enhanced by combining it with other genes which positively affect starch and/or oil content. For example, a gene which will increase ADPglucose pyrophosphorylase (ADPGPP) activity in plants may be used in combination with an SP gene to increase starch. Such ADPGPP genes include the *E. coli* glgC gene and its mutant glgC16. WO 91/19806 discloses how to incorporate this gene into many plant species in order to increase starch and/or solids.

Another gene which can be combined with SP to increase starch is a gene for sucrose phosphate synthase (SPS) which can be obtained from plants. WO 92/16631 discloses one such gene and its use in transgenic plants.

Another gene which can be combined with SP to increase oil is a gene for acetyl CoA carboxylase, which can be obtained from plants. WO 93/11243 discloses one such gene.

Plant Transformation/Regeneration

Plants which can be made to have increased polysaccharide (e.g. starch) content by practice of the present invention include, but are not limited to, maize, wheat, rice, tomato, potato, sweet potato, peanut, barley, cotton, strawberry, raspberry, and cassava. Plants which can be made to have modified carbohydrate content by practice of the present invention include, but are not limited to, maize, wheat. rice, tomato, potato, sweet potato, peanut, barley, sugarbeet, sugarcane, apple, pear, orange, grape, cotton, strawberry, raspberry, and cassava. Plants which can be made to have reduced bruising discoloration by practice of the present invention include, but are not limited to, wheat, potato, sweet potato, barley, sugarbeet, sugarcane, apple, pear, peach, orange, grape, banana, plantain, and cassava. Plants which can be made to have improved uniform solids content by practice of the present invention include, but are not limited to potato, sweet potato, banana, plantain, and cassava. Plants which can be made to have increased yield of harvested material by practice of the present invention include, but are not limited to, maize, wheat, rice, tomato, potato, sweet potato, peanut, barley, sugarbeet, sugarcane, apple, pear, orange, peach, banana, plantain, grape, cotton, strawberry, raspberry, and cassava. Plants which can be made to have decreased sucrose leading to increased oil or protein content include soybean, maize, canola, and sunflower.

A double-stranded DNA molecule of the present invention containing an SP gene can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1984), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A plasmid expression vector, suitable for the introduction of an SP gene in monocots using microprojectile bombardment is composed of the following: a promoter that is specific or enhanced for expression in the starch storage tissues in monocots, generally the endosperm, such as promoters for the zein genes found in the maize endosperm (Pedersen et al., 1982); an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., 1983). This expression cassette may be assembled on high copy replicons suitable for the production of large quantities of DNA.

A particularly useful Agrobacterium-based plant transformation vector for use in transformation of dicotyledonous plants is plasmid vector pMON530 (Rogers, S. G., 1987). Plasmid pMON530 is a derivative of pMON505 prepared by transferring the 2.3 kb StuI-HindIII fragment of pMON316 (Rogers, S. G., 1987) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers, S. G., 1987) in which the Ti plasmid homology region, LIH, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into Agrobacterium using the tri-parental mating procedure (Horsch & Klee, 1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/ streptomycin resistance determinant for selection in *E. coli* and *A. tumefaciens*, an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome.

One end of the integrated DNA is located between the right border sequence and the nopaline synthase gene and the other end is between the border sequence and the pBR322 sequences.

Another particularly useful Ti plasmid cassette vector is pMON-17227. This vector is described by Barry et al. in WO 92/04449 (corresponding to U.S. Ser. No. 07/749,611, incorporated herein by reference) and contains a gene encoding an enzyme conferring glyphosate resistance (denominated CP4) which is an excellent selection marker gene for many plants, including potato and tomato. The gene is fused to the Arabidopsis EPSPS chloroplast transit peptide (CTP2) and expressed from the FMV promoter as described therein.

When adequate numbers of cells (or protoplasts) containing the SP gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/ rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., Ammirato, 1984; Shimamoto, 1989; Fromm, 1990; Vasil, 1990; Vasil, 1992; Hayashimoto, 1989; Shimamoto, 1989; and Datta, 1990.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLES

Example 1

All basic DNA manipulations such as PCR, agarose electrophoresis, restriction digests, ligations, and *E. coli* transformations were performed by standard protocols as described in Sambrook et al.

A sucrose phosphorylase gene, gtfA, was generated by PCR amplification from *Streptococcus mutans* cells. The gene was amplified using the 5' oligonucleotide 5'CCCGGATCCATGGCAATTACAAATAAAAC (SEQ ID NO:1) and the 3' oligonucleotide

5'GGGGAGCTCACTCGAAGCTTATTGTTTGAT-CATTTTCTG (SEQ ID NO:2)

The PCR cycling conditions were as follows: 94° C., 3'; 55° C., 2'; 72° C., 2' (5 cycles); 94° C. 1'; 55° C. 2'; 72° C. 2' (30 cycles). The 1462 bp PCR product was purified using the GeneClean purification system (Bio101, Vista, Calif.), digested with BamHI and SacI, and ligated into the BamHI and SacI sites of pUC119. The ligated DNA was transformed into JM101 and a blue-white screen was used to identify colonies for plasmid preparation and restriction digestion. Digestion with HindIII was used to screen for transformants containing the gtfA gene. Clones with correct restriction patterns were screened for phenotypic expression by the ability to utilize sucrose as sole carbon source as follows: clones were transformed into a gal-*E. coli* strain, SK1592, and grown on minimal medium containing raffinose (which is taken up and hydrolyzed to galactose and sucrose) and an active clone was identified and named pMON17353.

An expression cassette was constructed to allow for constitutive expression of gtfA in plants. A fragment containing the enhanced 35S promoter (Kay, R. 1987), the Nopaline synthase 3' region (Bevan, M. 1984), and the pUC vector backbone was prepared from pMON999 (Rogers et al., 1987a) by restriction digestion with BglII and SacI. A fragment containing the gtfA coding region was prepared from pMON17353 by restriction digestion with BamHI and SacI. The correct fragments were separated by agarose gel electrophoresis and purified by the GeneClean procedure. The fragments were ligated, transformed into E. coli JM101, and putative recombinant plasmids were screened by restriction digestion with NotI. One clone was identified and named pMON17359.

A second expression cassette was constructed to direct expression of gtfA to the potato tuber. A fragment containing the patatin 1.0 promoter (described above), the Nopaline synthase 3' region, and the pUC vector backbone was prepared from an intermediate vector by restriction digestion with BamHI and SacI. An expression cassette was also constructed to direct expression of gtfA to the tomato fruit. A fragment containing the TFM7 promoter, the Nopaline synthase 3' region, and the pUC vector backbone was prepared from pMON16987 (PCT Application PCTUS94/07072, filed Jun. 27, 1994), which is derived from pMON999 but contains the TFM7 promoter, by restriction digestion with BglII and SacI. The correct fragments were separated by agarose gel electrophoresis and purified by the GeneClean procedure. These fragments were each ligated to the BamHI and SacI fragment from pMON17353. Transformation and screening of clones were as described above. Clones were designated as correct and named pMON17356 (Pat1.0/gtfA/NOS) and pMON17389 (TFM7/gtfA/NOS).

A third expression cassette was constructed to direct expression of gtfA to the potato tuber using a 3.5 kb promoter of patatin. The patatin 3.5 promoter was obtained from the plasmid pBI240.7 (Bevan et al., 1986). The majority of the 3.5 promoter was excised from pBI240.7, from the HindIII site (at ~−3500) to the XbaI site at −337, and combined with the remainder of the promoter, from the XbaI site to a BglII site at +22 (formerly a DraI site), in a triple ligation into a vector which provided a BglII site to form pMON17280. An intermediate vector was prepared by digestion of pMON17353 with BamHI/SacI and insertion of the fragment into pBS. This vector was then digested with EcoRI and SacI. pMON17280 was digested with EcoRI and SacI resulted in a fragment containing the patatin 3.5 promoter, the Nopaline synthase 3' region, and the pUC vector backbone. The correct sized fragments were obtained by agarose gel electrophoresis and the GeneClean procedure. The fragments were ligated, transformed into E. coli JM101, and screened by restriction digestion with HindIII. One clone was designated as correct and named pMON17495.

In pMON17356, pMON17359, pMON17389, and pMON17495, the promoter, gtfA gene and the Nos 3' region can be isolated on a NotI restriction fragment. These fragments can then be inserted into a unique NotI site of either vector pMON17227 (described above) or pMON17320 to construct glyphosate selectable plant transformation vectors. pMON17320 is a pMON17227 derivative which also contains a Ppatatin 1.0/CTP1-glgC16 cassette. The CTP1-glgC16 fusion encodes a modified ADPglucose pyrophosphorylase as described by Kishore in WO 91/19806. A vector was also constructed for tomato expression of GtfA by combining the gtfA gene and 3' region from pMON17356 with the ~2.0 kp potato small ADPglucose pyrophosphorylase subunit gene promoter (See U.S. Ser. No. 08/344,639, Barry et al., filed Nov. 4, 1994, incorporated herein by reference.) in a plant transformation vector to form pMON17486.

The vector DNA is prepared by digestion with NotI followed by treatment with calf intestinal alkaline phosphatase (CIAP). The gtfA containing fragments are prepared by digestion with NotI, agarose gel electrophoresis and purification with GeneClean. Vector and insert DNA is ligated, transformed into the E. coli strain LE392, and transformants were screened by restriction digestion to identify clones containing the gtfA expression cassettes. Clones in which transcription from the gtfA cassette is in the same direction as transcription from the selectable marker were designated as correct and named pMON17357 (FMV/CP4/E9, Pat1.0/gtfA/NOS), pMON17358 (Pat1.0/CTP1-glgC16/E9, Pat1.0/gtfA/NOS, FMV/CP4/E9), pMON17360 (FMV/CP4/E9, E35S/gtfA/NOS), pMON17390 (FMV/CP4/E9, TFM7/gtfA/NOS), pMON17392 (Pat1.0/CTP1-glgC16/E9, TFM7/gtfA/NOS, FMV/CP4/E9), and pMON17496 (FMV/CP4/E9, Pat3.5/gtfA/NOS).

A transformation vector was constructed to direct expression of gtfA in maize seed. A fragment containing the glutelin promoter Osgt-1, Hsp70 intron (described above), Nopaline synthase 3' region, kanamycin resistance, and pUC backbone was prepared by restriction digestion, agarose gel electrophoresis, and GeneClean. A fragment containing the gtfA coding region was prepared from pMON17359 by restriction digestion with NcoI and NotI. The fragments were ligated, transformed and screened by restriction digestion. A correct clone was identified and named pMON24502 (Osgt1/Hsp70/gtfA/NOS).

A transformation vector was constructed to direct expression of gtfA in seeds of oilseed crops. A BamHI-EcoRI fragment of pMON17353 was ligated into the BglII-EcoRI sites of an intermediate vector to give pMON26104 which placed the gtfA gene behind the 7s promoter (discussed above) and used the E9 3' terminator sequence. A NotI fragment containing the FMV promoter, the fusion of the CTP2 and glyphosate resistance gene and a Nos 3' sequence, was ligated into the NotI site of pMON26104 to give pMON26106, a double border plant transformation vector with both of the cassettes in the same orientation.

Example 2

The vector pMON17357 was transformed into Russet Burbank potato callus following the method described by Barry et al. in WO 94/28149 for glyphosate selection of transformed lines. A number of lines were obtained and evaluated in field tests. The results of this test are shown in Table 1. As can be seen therein several lines were identified as containing higher starch levels (measured as total solids) and some of those had decreased bruising.

TABLE 1

| Line Identification | Solids (%) Mean | Bruising Index Mean |
|---|---|---|
| Control | 21.9 | 3.399 |
| 1 | 22.9 | 3.798 |
| 3 | 22.2 | 3.479 |
| 4 | 23.3 | 2.899 |
| 6 | 21.8 | 2.798 |
| 8 | 22.7 | 2.979 |
| 11 | 21.6 | 2.968 |
| 12 | 22.0 | 3.383 |

TABLE 1-continued

| Line Identification | Solids (%) Mean | Bruising Index Mean |
|---|---|---|
| 14 | 22.3 | 3.218 |
| 15 | 22.7 | 2.979 |
| 17 | 22.3 | 3.394 |
| 18 | 21.7 | 3.394 |
| 19 | 22.4 | 3.213 |
| 22 | 22.7 | 3.503 |

Tubers from twelve lines were tested for any change in the distribution of starch between the pith or cortex. This was accomplished by peeling the tubers, cutting them into strips resembling french fries, and measuring the solids using a brine flotation comparison test. The average solid level for strips from the pith was subtracted from the average solids level for strips from the cortex. Thus a difference in solids which is less than that for the control (4.61% in this test) is an indication of more uniform distribution of starch in the tuber, which is highly desirable. The results are shown in Table 2. As can be seen, the difference in solids between the cortex and the pith was reduced in ten of the twelve lines.

TABLE 2

| Line | Solids Difference (%) |
|---|---|
| Control | 4.61 |
| 3 | 4.53 |
| 4 | 4.16 |
| 6 | 3.57 |
| 8 | 3.20 |
| 11 | 3.94 |
| 12 | 4.39 |
| 14 | 4.67 |
| 15 | 3.56 |
| 17 | 2.61 |
| 18 | 3.79 |
| 19 | 5.19 |
| 22 | 3.92 |

Five of these lines were tested the next year in the field, four of them in multiple locations. (Line number 8 was tested in only one location.) The absolute increase in solids in those five lines, indicating an increase in starch content, was again demonstrated in each line. The results are shown in Table 3.

TABLE 3

| Line | Solids increase |
|---|---|
| 1 | 0.256 |
| 4 | 0.856 |
| 8 | 2.61 |
| 15 | 0.211 |
| 22 | 0.162 |

Example 3

Expression of gtfA in corn introduces a novel catalytic activity which may facilitate sucrose import into the endosperm by creating a steeper concentration gradient and conserve energy since the equivalent of one mole of ATP is normally required to convert sucrose to a hexose plus a hexose phosphate. The vector pMON24502 has been introduced into maize cells by microprojectile bombardment using two different types of embryogenic callus tissue for transformation. It was cotransformed with either (1) pMON19476 which contains a selection cassette of the enhanced 35S promoter, the Hsp70 intron, the NPTII coding sequence for kanamycin resistance, and the nos 3' sequence or (2) pMON19336 which contains two selection cassettes for glyphosate resistance, each using the rice actin promoter and the Hsp70 intron, but one uses a gene encoding glyphosate oxidase and one uses the CP4 glyphosate resistance gene.

(1) Immature maize embryos (H99 genotype) were isolated as described in EP 586 355 A2. Embryogenic callus was obtained by culturing the immature embryos for about two weeks on the medium described by Duncan et al. (1985), called Medium D. After 2 weeks, callus (Type I) is obtained and is maintained by subculturing every 2–3 weeks onto fresh Medium D. Approximately four hours prior to bombardment, actively growing callus (mid subculture cycle) is placed on Medium D with added mannitol and sorbitol for osmotic pretreatment. Approximately 16–24 hours after bombardment with particles coated with pMON24502 and pMON19476, the tissue is placed on Medium D without mannitol or sorbitol. Approximately two days later, the tissue is transferred onto Medium D containing paromomycin. Resistant tissue is transferred to fresh Medium D with paromomycin at approximately three week intervals. Plant regeneration is accomplished on Medium D with 6-benzylaminopurine (without dicamba) for a 3–6 day "pulse", followed by placement on MS medium without hormones.

(2) Type II callus, derived from immature embryos of the "Hi-II" genotype, is used by following the method of Dennehy et al., 1994. Type II callus was pretreated on N6 1-100-25 medium containing 0.4M mannitol+sorbitol (0.2M of each) for four hours prior to bombardment with pMON24502 and pMON19336 and left on this same medium for 16 to 24 hours after bombardment. The tissue was then transferred to N6 1-100-25 medium without added mannitol or sorbitol. Selection was accomplished using 1–3 mM glyphosate in N6 1-0-25 medium (containing no casamino acids).

Fertile maize plants have been obtained by each method and their seeds tested. Expression of the gtfA gene was confirmed by Western blot analysis using goat antibody raised against $E.$ $coli$-expressed gtfA. Of the 16 lines screened for expression, 9 have been shown to express gtfA at approximately 0.05 to 0.5% of the total cellular protein. The starch biosynthetic rate in maize endosperm tissue expressing GtfA (sucrose phosphorylase) was measured in vitro using a sugar feeding assay which has been described previously (Felker, et al., 1990). Field grown plants were screened by PCR to identify the positive and negative segregants. Positive and control ears from two GtfA transformed lines (Knowl and De) were harvested at 20 to 22 days post pollination, at the time of linear grain fill. Endosperm sections were recovered and were fed $^{14}$C-sucrose at concentrations of 50 and 200 mM. The 200 mM concentration is the most physiologically relevant but due to the lower Km of GtfA for sucrose than the endogenous enzymes, the lower concentration (50 mM) was used to improve the likelihood of measuring an effect from GtfA. Time points were taken at one and two hours after feeding $^{14}$C and the radioactivity incorporated into the starch fraction was determined. The results with the two lines, are summarized in the following Table (data reported as average counts incorporated into starch fraction):

TABLE 4A

Feeding with 50 mM sucrose

| time of sampling | control | Knowl |
|---|---|---|
| 1 hr | 9033 | 20895 |
| 2 hr | 15947 | 26695 |
| | control | De |
| 1 hr | 10909 | 10860 |
| 2 hr | 19193 | 24284 |

TABLE 4B

Feeding with 200 mM sucrose

| time of sampling | control | Knowl |
|---|---|---|
| 1 hr | 9880 | 12980 |
| 2 hr | 11175 | 21407 |
| | control | De |
| 1 hr | 7703 | 7471 |
| 2 hr | 11038 | 13007 |

The results demonstrate that corn endosperm tissues expressing GtfA can produce starch at a more rapid rate (two-fold) than controls. The differences in starch rate are more apparent at the lower substrate concentrations, potentially due to the differences in substrate kinetics between GtfA and the endogenous sucrose synthase. Differences were also noted when comparing the effects in the lines De and Knowl, with Knowl displaying a more positive effect. GtfA expression is very high in Knowl, in the range of 0.5% of the total protein, whereas GtfA expression in De is in the range of 0.05%. The differences in starch biosynthetic rates are likely a function of GtfA expression levels.

Example 4

The vector pMON26106 has been introduced into canola and soybean callus via Agrobacterium transformation (Hinchee et al.). After selection of transformed cells using glyphosate and regeneration into whole plants, the seeds set by those plants will be analyzed.

Example 5

The vector pMON24502 has been introduced into wheat cells by microprojectile bombardment. Immature wheat embryos were isolated as described by Vasil et al. (1993). Embryogenic callus was obtained by culturing the immature embryos for 4 to 7 days, on a modified MS medium comprising about 40 g/l maltose and about 2 mg/l 2,4-D. The callus was subjected to bombardment with microprojectiles coated with pMON24502 and a plasmid containing a bialophos resistance gene. One day after bombardment the immature embryos were transferred to a growth medium containing the selective agent bialaphos. After seven days on the growth and selective medium the immature embryo-derived callus was removed to a shoot-producing medium (modified MS medium no 2,4-D) containing bialophos and grown for 28–40 days. A PCR assay will be done to confirm that the gtfA gene is present in the shoots. Shoots containing the gtfA gene will be rooted and taken to soil. When transformed plants are recovered and grown to maturity, their seeds will exhibit increased starch levels.

Example 6

The vector pMON24502 may be introduced into rice cells by microprojectile bombardment. Upon regeneration and selection, transformed plants will be assayed for expression of the gtfA gene and those plants demonstrating high expression will be grown to maturity. The seeds of the mature plants will exhibit increased starch levels.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Ammirato, P. V., et al. *Handbook of Plant Cell Culture—Crop Species*. Macmillan Publ. Co. (1984).
Benfey, P., Ren, L., and Chua, N. H. (1989) *EMBO J*, 5: 2195–2202.
Bevan, M. (1984) *Nucleic Acids Res*. 12 (22): 8711–8721.
Bevan, et al. (1986) *Nucleic Acids Res*. 14 (11):4625–4638.
Blennow, A. and Johansson, G. (1991) *Phytochemistry* 30:437–444.
Datta, et al. (1990) *Biotechnology* 8:736–740.
Deikman, J. and R. L. Fischer. (1988) *EMBO J* 7: 3315–3320.
Dennehy et al. (1994) *Plant Cell Tiss. & Organ Cult*. 36:1–7.
Duncan et al. (1985) *Planta* 165:322–332.
Ebbelaar, et al. (1993) Int. Symp. on Gen. Manip. of Plant Metabolism and Growth, 29–31 March, Norwich UK, Abstract #9.
Felker, F. C., Liu, K. C., and Shannon, J. C. (1990) *Plant Physiology* 94, 996–1001.
Ferretti, et al. (1988) *Infection and Immun*. 56:1585–1588.
Fournier, et al. (1994) *Mol. Plant-Microbe Inter*. 7:164–172.
Fraley, et al. (1983). *PNAS USA* 80: 4803–4807.
Fraley, et al. (1985). *Bio/Technology* 3:629–635.
Fraley, et al. (1986). *Critical Reviews in Plant Sciences* 4: 1–46.
Fromm et al. (1990) *Bio/Technology* 8: 833–839.
Fromm, M., (1990) UCLA Symposium on Molecular Strategies for Crop Improvement, Apr. 16–22, 1990. Keystone, Colo.
Hannapel, D. J. (1990) *Plant Phys*. 94: 919–925.
Hayashimoto, A., Z. Li, Murai, N. (1990) *Plant Physiol*. 93:857–863.
Herrera-Estrella, L., et al. (1983) *Nature* 303:209.
Hinchee et al. (1988) *Biotechnology* 6:915–922.
Horsch, R. B. and H. Klee. (1986) *PNAS U.S.A*. 83:4428–32.
Iglesias, et al., (1993) *J. Biol Chem*. 268:1081–1086.
Jefferson, et al. (1990) *Plant Mol. Biol*. 14: 995–1006.
Kay, R., A. Chan, M. Daly and J. McPherson. (1987) *Science* 236:1299–1302.
Kitao, S. and E. Nakano (1992) *J. Ferment. Bioeng*. 73:179–84.

Klee, H. J., et al. (1985) *Bio/Technology* 3:637–42.
Klee, H. J., and Rogers, S. G. (1989). Plant gene vectors and genetic transformation: plant transformation systems based on the use of *Agrobacterium tumefaciens*. Cell Culture and Somatic Cell, Genetics of Plants 6, 1–23.
Klein et al. (1989) *Bio/Technology* 6: 559–563.
Kossmann et al. (1991) *Mol. Gen. Genet.* 230:39–44.
Mignery, et al (1988) *Gene* 62:27–44.
Mori et al. (1991) *J. Biol. Chem.* 266: 18446–18453.
Muller, et al (1990) *Mol. Gen. Genet.* 224:136–146.
Nakamura, K., and Matsuoka, K. (1993) *Plant Physiol.* 101:1–5.
Nakano et al. (1989) *J. Biochem.* 106: 691–695.
Ohta et al. (1991) *Mol. Gen. Genet.* 225: 369–378.
Ohshima et al. (1990) *Nucleic Acid Research* 18: 181.
Pear, et al. (1989) *Plant Mol. Biol.* 13 :639–651.
Pedersen, et al. (1982) *Cell* 29: 1015–1026.
Perry, D. and H. K. Kuramitsu (1990) *Infect. Immun.* 58(10):3462–4.
Pimentel, et al. (1992) *Revista de Microbiologia* 23:199–205.
Robeson, et al. (1983) *J. Bacteriol.* 153:211–221.
Rocha-Sosa, et al. (1989) *EMBO J.* 8 (1):23–29.
Rogers, S. G., H. J. Klee, R. B. Horsch, and R. T. Fraley. (1987a) *Improved Vectors for Plant Transformation: Expression Cassette Vectors and new Selectable Markers.* In *Methods in Enzymology*. Edited by R. Wu and L. Grossman. 253–277. San Diego: Academic Press.
Rogers, S., et al. (1987) In 153 *Methods in Enzymology*. Edited by H. Weissbach and A. Weissbach. 253: Academic Press.
Rogers, S., and Klee, H. (1987). Pathways to genetic manipulation employing Agrobacterium. *Plant Gene Research*, Plant DNA Infectious Agents, Vol IV. Hohn, T. and J. Schell, eds. Springer-Verlag, Vienna, 179–203.
Rohde et al. (1990) *J. Genet. & Breed.* 44:311–315.
Russell, et al. (1988) *Infect. Immun.* 56(10):2763–5.
Samac, et al. (1990) *Plant Physiol.* 93:907–914.
Sambrook et al., *Molecular cloning: A laboratory manual*, 2nd ed., Cold Spring Harbor Laboratory Press, Cold Spring Harbor, N.Y., 1989.
Schmidhauser, T. J. and D. R. Helinski. (1985) *J. Bacteriol.* 164–155.
Shahar et al. (1992) *Plant Cell* 4:135–147.
Shimamoto, K. et al. (1989) *Nature* 338:274–276.
Silverstein, R., et al. (1967) *J. Biol. Chem.* 242:1338–1346.
Solanoubat, M. and G. Belliard (1987) *Gene* 60:47–56.
Solanoubat, M. and G. Belliard (1989) *Gene* 84:181–185.
Sonnewald et al. (1991) *Plant J.* 1:95–106.
Stiekema et al. (1988) *Plant Mol. Biol.* 11: 255–269.
Stukerlj et al. (1990) *Nucl. Acids Res.* 18:46050.
Takaha et al., (1993) *J. Biol. Chem.* 26 8:1391–1396.
Tierney, et al. (1987) *Planta* 172:356–363.
Vandamme, et al. (1987) *Adv. Appl. Microbiol.* 32:163–201.
Vasil, V., F. Redway and I. Vasil. (1990) *Bio/Technology* 8:429–434.
Vasil et al. (1992) *Bio/Technology* 10:667–674.
Vasil et al. (1993) *Bio/Technology* 11: 1153–1158.
Yoshida et al. (1992) *Gene* 10: 255–259.
Zheng et al. (1993) *Plant J.* 4: 3357–366.

What is claimed is:

1. A transformed plant cell comprising a recombinant, double-stranded DNA molecule comprising in sequence:
   (a) a promoter which functions in said plant cell;
   (b) a structural DNA sequence that causes the production of an RNA sequence which encodes a sucrose phosphorylase enzyme; and
   (c) a 3' non-translated region which functions in plant cells to cause transcriptional termination and the addition of polyadenylated nucleotides to the 3' end of the RNA sequence.

2. The plant cell of claim 1, wherein said plant cell is selected from the group consisting of a potato plant cell, a maize plant cell, a rice plant cell, a wheat plant cell, a tomato plant cell, a barley plant cell, a sugarbeet plant cell, a sweetpotato plant cell, a peanut plant cell, a sugarcane plant cell, a grape plant cell, a pear plant cell, an apple plant cell, an orange plant cell, a cassava plant cell, a banana plant cell, a plantain plant cell, and a peach plant cell.

3. A transgenic plant regenerated from the transformed plant cell of claim 1.

4. A seed obtained from transgenic plant of claim 3, wherein said seed contains a recombinant, double-stranded DNA molecule comprising in sequence:
   a) a promoter which functions in said plant cell;
   b) a structural DNA sequence that causes the production of an RNA sequence which encodes for a sucrose phosphorylase enzyme; and
   c) a 3' non-translated region, which functions in plant cells to cause transcriptional termination and the addition of polyadenylated nucleotides to the 3' end of the RNA sequence.

5. A method of harvesting a plant grown from the seed from claim 4, comprising:
   a) growing plants from said seed; and
   b) harvesting said plants.

* * * * *